US00PP32707P3

(12) United States Plant Patent
Post

(10) Patent No.: US PP32,707 P3
(45) Date of Patent: Dec. 29, 2020

(54) ***CHRYSANTHEMUM* PLANT NAMED 'DLFALLI5'**

(50) Latin Name: ***Chrysanthemum* X *morifolium***
Varietal Denomination: DLFALLI5

(71) Applicant: Arie Gerard Post, Delft (NL)

(72) Inventor: Arie Gerard Post, Delft (NL)

(73) Assignee: DELIFLOR ROYALTIES B.V., Maasdijk (NL)

( * ) Notice: Subject to any disclaimer, the term of this patent is extended or adjusted under 35 U.S.C. 154(b) by 0 days.

(21) Appl. No.: 16/873,326

(22) Filed: Mar. 19, 2020

(65) Prior Publication Data

US 2020/0305322 P1 Sep. 24, 2020

Related U.S. Application Data

(60) Provisional application No. 62/919,611, filed on Mar. 20, 2019.

(51) Int. Cl.
*A01H 5/02* (2018.01)
*A01H 6/14* (2018.01)

(52) U.S. Cl.
USPC ..... Plt./286
CPC ..... *A01H 6/1424* (2018.05)

(58) Field of Classification Search
USPC ..... Plt./263.1, 284, 286
See application file for complete search history.

(56) References Cited

U.S. PATENT DOCUMENTS

PP22,923 P2 * 8/2012 Dekker ..... A01H 6/1424 Plt./287

* cited by examiner

*Primary Examiner* — Susan McCormick Ewoldt
*Assistant Examiner* — Karen M Redden
(74) *Attorney, Agent, or Firm* — C. A. Whealy

(57) ABSTRACT

A new and distinct cultivar of *Chrysanthemum* plant named 'DLFALLI5', characterized by its upright plant habit; vigorous growth habit; freely branching habit; dark green-colored leaves; uniform and freely flowering habit; strong upright flowering stems with numerous inflorescences; pom-pom-type inflorescences with yellow green-colored ray florets; relative tolerance to low production temperatures.

2 Drawing Sheets

Figure 1:
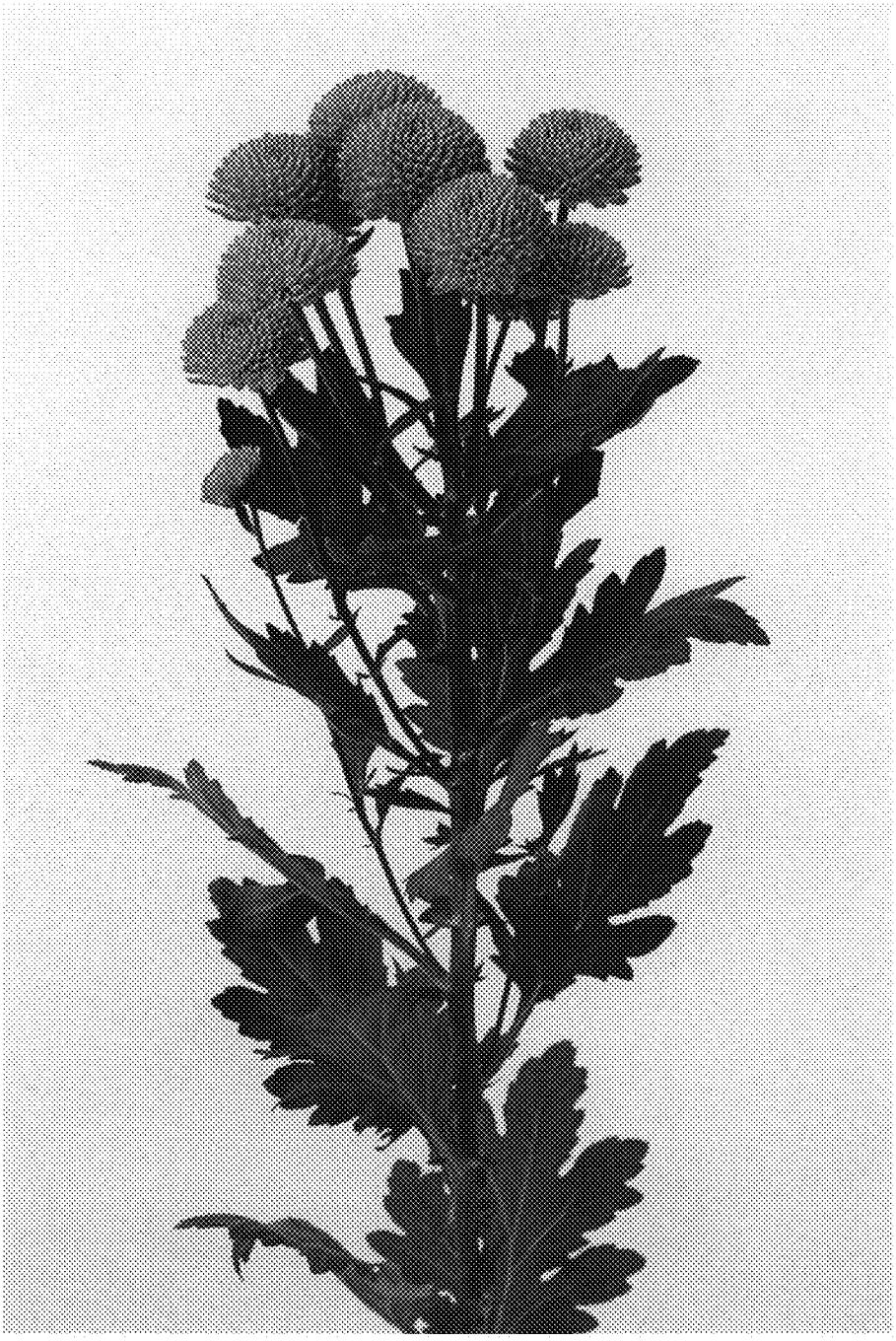

Botanical designation: *Chrysanthemum* X *morifolium*.
Cultivar denomination: 'DLFALLI5'.

STATEMENT REGARDING PRIOR DISCLOSURES BY INVENTOR/APPLICANT & ASSIGNEE

An European Community Plant Breeder's Rights application for the instant plant was filed by the Assignee, Deliflor Royalties B. V. of Maasdijk, The Netherlands on Feb. 1, 2019, application number 2019/0352. Foreign priority is not claimed to this application.

The Inventor/Applicant and Assignee assert that no publications nor advertisements relating to sales, offers for sale or public distribution occurred more than one year prior to the effective filing date of this application. Any information about the claimed plant would have been obtained from a direct or indirect disclosure from the Inventor/Applicant and/or the Assignee. Inventor/Applicant and Assignee claim a prior art exemption under 35 U.S.C. 102(b)(1) for disclosure and/or sales prior to the filing date but less than one year prior to the effective filing date.

BACKGROUND OF THE INVENTION

The present invention relates to a new and distinct cultivar of *Chrysanthemum* plant, botanically known as *Chrysanthemum* x *morifolium*, typically grown as a cut flower *Chrysanthemum* and hereinafter referred to by the name 'DLFALLI5'.

The new *Chrysanthemum* plant is a product of a planned breeding program conducted by the Inventor in Maasdijk, The Netherlands. The objective of the breeding program is to create new cut flower *Chrysanthemum* plants with numerous attractive inflorescences.

The new *Chrysanthemum* plant originated from a cross-pollination in January, 2015 of a proprietary selection of *Chrysanthemum* x *morifolium* identified as code number DB 10061, not patented, as the female, or seed, parent with a proprietary selection of *Chrysanthemum* x *morifolium* identified as code number DB 49880, not patented, as the male, or pollen, parent. The new *Chrysanthemum* plant was discovered and selected as a single flowering plant from within the progeny of the stated cross-pollination in a controlled greenhouse environment in Maasdijk, The Netherlands in September, 2015.

Asexual reproduction of the new *Chrysanthemum* plant by vegetative terminal cuttings since September, 2015 in Maasdijk, The Netherlands, has shown that the unique features of this new *Chrysanthemum* plant are stable and reproduced true to type in successive generations of asexual reproduction.

SUMMARY OF THE INVENTION

Plants of the new *Chrysanthemum* have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'DLFALLI5'. These characteristics in combination distinguish 'DLFALLI5' as a new and distinct *Chrysanthemum* plant:

1. Upright plant habit; vigorous growth habit.
2. Freely branching habit.
3. Dark green-colored leaves.
4. Uniform and freely flowering habit.
5. Strong upright flowering stems with numerous inflorescences.
6. Pompom-type inflorescences with yellow green-colored ray florets.
7. Relatively tolerant to low production temperatures.

Plants of the new *Chrysanthemum* differ from plants of the female parent selection in ray floret color as ray florets of plants of the new *Chrysanthemum* are darker yellow green in color than ray florets of plants of the female parent selection. In addition, leaf sinuses of plants of the new *Chrysanthemum* are more parallel than and not as convergent as leaf sinuses of plants of the female parent selection.

Plants of the new *Chrysanthemum* differ from plants of the male parent selection in ray floret shape as ray florets of plants of the new *Chrysanthemum* have obtuse apices whereas ray florets of plants of the male parent selection have emarginate apices. In addition, leaf sinuses of plants of the new *Chrysanthemum* are more parallel than and not as convergent as leaf sinuses of plants of the male parent selection.

Plants of the new *Chrysanthemum* can be compared to plants of *Chrysanthemum* X *morifolium* 'Deliolive', not patented. In side-by-side comparisons plants of the new *Chrysanthemum* differ primarily from plants of 'Deliolive' in ray floret color as ray florets of plants of the new *Chrysanthemum* are darker yellow green in color than ray florets of plants of 'Deliolive'. In addition, ray florets of plants of the new *Chrysanthemum* are more incurved than ray florets of plants of 'Deliolive'.

Plants of the new *Chrysanthemum* can also be compared to plants of *Chrysanthemum* X *morifolium* 'Dekgrassly', disclosed in U.S. Plant Pat. No. 22,923. In side-by-side comparisons plants of the new *Chrysanthemum* differ primarily from plants of 'Dekgrassly' in ray floret color as ray florets of plants of the new *Chrysanthemum* are darker yellow green in color than ray florets of plants of 'Dekgrassly'. In addition, inflorescences of plants of the new *Chrysanthemum* are larger and have fewer ray florets than inflorescences of plants of 'Dekgrassly'.

BRIEF DESCRIPTION OF THE PHOTOGRAPHS

The accompanying photographs illustrate the overall appearance of the new *Chrysanthemum* plant showing the colors as true as it is reasonably possible to obtain in colored reproductions of this type.

The photograph on the first sheet (FIG. 1 of 2) comprises a side perspective view of a typical flowering stem of 'DLFALLI5' grown as a spray-type cut flower.

Figure 2:
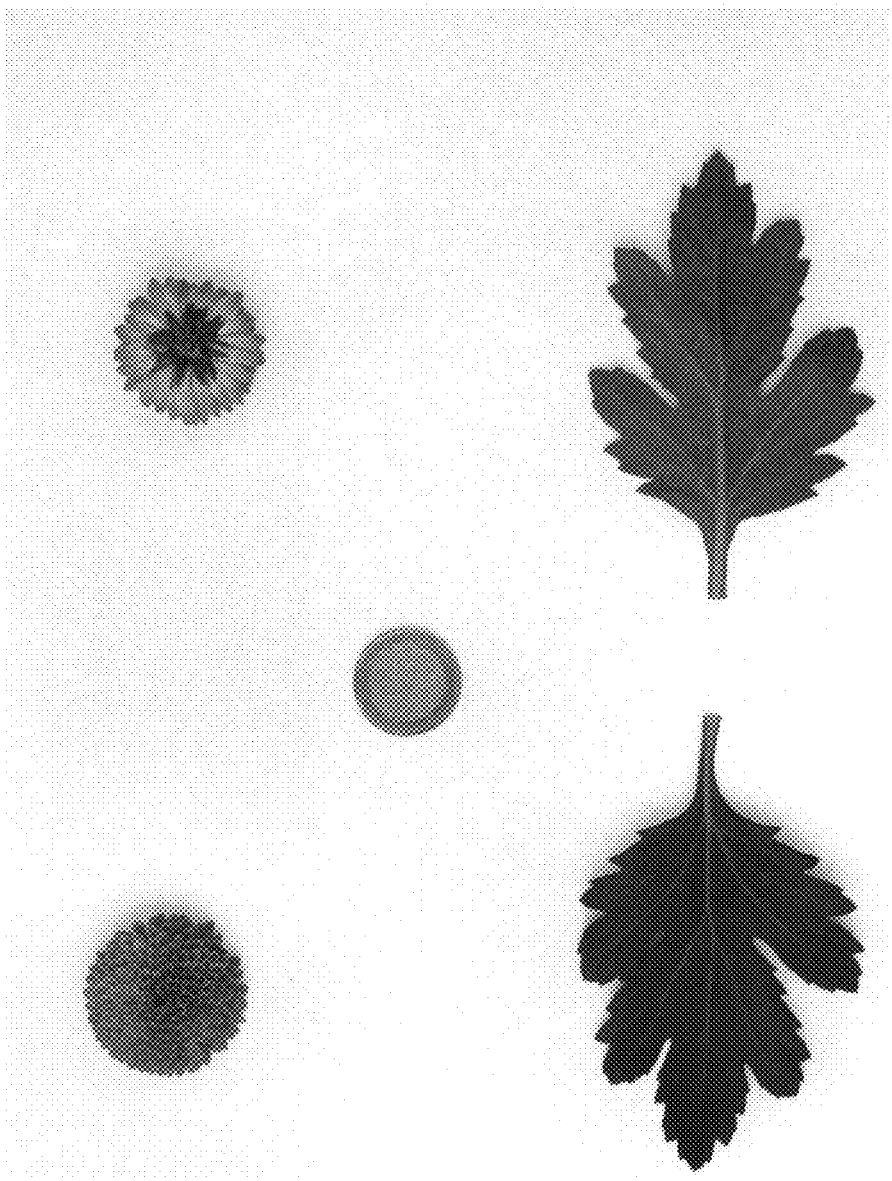

The photograph on the second sheet (FIG. 2 of 2) is a close-up view of lower (top of the photographic sheet) and upper (bottom of the photographic sheet) surfaces of typical inflorescences (left) and leaves (right).

DETAILED BOTANICAL DESCRIPTION

The aforementioned photographs and following observations and measurements describe plants grown during the winter in ground beds in a glass-covered greenhouse in Maasdijk, The Netherlands and under cultural practices typical of commercial cut *Chrysanthemum* production. Plants were initially given long day/short night treatments followed by short day/long night treatments to induce flower initiation and development. During the production of the plants, day temperatures ranged from 18° C. to 25° C., night temperatures ranged from 2° C. to 20° C. and light levels averaged 8 klux. Plants were grown as single-stem spray-type plants and were nine weeks old when the photographs and the description were taken. In the following description, color references are made to The Royal Horticultural Society Colour Chart, 2015 Edition, except where general terms of ordinary dictionary significance are used.

Botanical classification: *Chrysanthemum* X *morifolium* 'DLFALLI5'.

Parentage:

*Female, or seed, parent*.—Proprietary selection of *Chrysanthemum* x *morifolium* identified as code number DB 10061, not patented.

*Male, or pollen, parent*.—Proprietary selection of *Chrysanthemum* x *morifolium* identified as code number DB 49880, not patented.

Propagation:

*Type*.—Terminal vegetative cuttings.

*Time to initiate roots, summer*.—About six days at temperatures about 24° C.

*Time to initiate roots, winter*.—About eight days at temperatures about 22° C.

*Time to produce a rooted young plant, summer*.—About twelve days at temperatures about 24° C.

*Time to produce a rooted young plant, winter*.—About two weeks at temperatures about 22° C.

*Root description*.—Fine, fibrous; typically creamy white in color, actual color of the roots is dependent on substrate composition, water quality, fertilizers, substrate temperature and physiological age of roots.

*Rooting habit*.—Freely branching, medium density.

Plant description:

*Plant and growth habit*.—Herbaceous decorative-type cut flower that is typically grown as a single stem spray-type; upright plant habit; vigorous growth habit and rapid growth rate.

*Plant height, soil level to top of foliar plane*.—About 77.8 cm.

*Plant height, soil level to top of inflorescence plane*.—About 81.5 cm.

*Plant (spray) diameter*.—About 19.9 cm.

*Flowering stem length*.—About 73.7 cm.

*Flowering stem diameter*.—About 5 mm.

*Flowering stem internode length*.—About 2.8 cm.

*Flowering stem strength*.—Strong.

*Flowering stem aspect*.—Erect.

*Flowering stem texture and luster*.—Sparsely pubescent; slightly glossy.

*Flowering stem color, developing*.—Close to 144B.

*Flowering stem color, developed*.—Close to 146D tinged with close to 148A; at the internodes, close to 146D.

*Leaf description*.—Arrangement: Alternate; simple. Length: About 11.2 cm. Width: About 7.6 cm. Shape: Ovate. Apex: Short apiculate. Base: Attenuate. Margin: Palmately lobed, coarsely serrate to crenate; sinuses parallel to convergent and medium in depth. Texture and luster, upper surface: Moderately pubescent, not rugose; moderately velvety; very slightly glossy. Texture and luster, lower surface: Moderately pubescent, prominent venation; slightly velvety; matte. Venation pattern: Pinnate, reticulate. Color: Developing leaves, upper surface: Close 137B. Developing leaves, lower surface: Close to 138B. Fully developed leaves, upper surface: Close to between NN137A and 147A; venation, close to 146B. Fully developed leaves, lower surface: Close to 147B; venation, close to 146C. Petioles: Length: About 1.8 cm. Diameter: About 2.5 mm by 3 mm. Strength: Moderately strong. Texture and luster, upper and lower surfaces: Moderately pubescent; slightly glossy. Color, upper surface: Close to 148B; edges, close to 137A. Color, lower surface: Close to 147C; edges, close to 137B. Stipules: Quantity and appearance: Two leafy stipules, opposite, at the petiole attachment to the stem. Length: About 8 mm. Width: About 8 mm. Shape: Broadly obovate to flabellate. Texture and luster, upper surface: Moderately pubescent, not rugose; moderately velvety; very slightly glossy. Texture and luster, lower surface: Moderately pubescent, prominent venation; slightly velvety; matte. Color, upper surface: Close to between NN137A and 147A. Color, lower surface: Close to 147B.

Inflorescence description:

*Appearance*.—Decorative inflorescence form with oblanceolate-shaped ray florets and tubular disc florets (disc florets are inconspicuous); inflorescences borne perpendicular to peduncles and face mostly upright to slightly outwardly; ray and disc florets develop acropetally on a capitulum.

*Fragrance*.—Faintly fragrant; typical of *Chrysanthemums*.

*Flowering response*.—Under natural conditions, plant flower in the autumn/winter in the Northern Hemisphere; at other times of the year, inflorescence initiation and development can be induced under short day/long night conditions (at least 13.5 hours of darkness); uniform flowering habit and short response time, plants exposed to two weeks of long day/short night conditions after planting followed by photoinductive short day/long night conditions flower about 49 days later when grown as a spray-type.

*Postproduction longevity*.—Good postproduction longevity; in an interior environment, inflorescences and foliage will maintain good color and substance for about two weeks; inflorescences persistent.

*Quantity of inflorescences*.—Freely flowering habit; when grown as a spray-type, about 19 inflorescences develop per flowering stem.

*Inflorescence size*.—Diameter: About 3.6 cm. Depth (height): About 2.3 cm. Disc diameter: About 4 mm.

*Receptacles*.—Height: About 4 mm. Diameter: About 5.5 mm. Shape: Flattened globular. Color: Close to 145B.

*Inflorescence buds*.—Height: About 7 mm. Diameter: About 1.3 cm. Shape: Broad disc-shaped. Texture and luster: Distally, smooth and glabrous; proximally, sparsely pubescent; matte. Color: Close to 137B to 137C; immature ray florets, close to 160B to 160C and between 163B and 163C.

*Ray florets*.—Quantity and arrangement: About 160 arranged in about seven whorls. Length: About 1.3 cm; varying between 1.2 cm and 1.4 cm. Width: About 3.5 mm; varying between 0.3 cm and 0.5 cm. Shape: Oblanceolate; moderately to slightly concave and slightly carinate. Apex: Obtuse. Base: Attenuate. Margin: Entire; not undulate. Aspect: Initially upright to about 40° from vertical. Texture and luster, upper surface: Smooth, glabrous; moderately velvety; matte. Texture and luster, lower surface: Smooth, glabrous; slightly velvety; matte. Color: When opening, upper and lower surfaces: Close to 145C. Fully opened, upper and lower surfaces: Close to 144A; venation, close to 144C; color does not change with development.

*Disc florets*.—Quantity and arrangement: About nine spirally arranged in about three whorls at the center of the receptacle; disc florets inconspicuous. Length: About 7 mm. Diameter: About 1 mm. Shape: Lower 85% fused into a tube; upper 15% free. Apex: Narrowly acute. Margin, distally: Entire. Texture and luster, inner and outer surfaces: Smooth, glabrous; glossy. Color, when opening and fully opened, inner and outer surfaces: Distally, close to N144D and proximally, close to 145C.

*Involucral bracts*.—Quantity and arrangement: About 22 arranged in two to three whorls. Length: About 7 mm. Width: About 4 mm. Shape: Ovate. Apex: Obtuse. Base: Cuneate. Margin: Entire. Texture and luster, upper surface: Smooth, glabrous; glossy. Texture and luster, lower surface: Sparsely pubescent; matte. Color, upper surface: Close to between 143A and 144A; margins, translucent and close to 157D and 200A. Color, lower surface: Close to 137B and 137C; margins, translucent and close to 157D and 200A.

*Peduncles*.—Length, terminal peduncle: About 6.1 cm. Diameter, terminal peduncle: About 3 mm. Length, third peduncle: About 7.6 cm. Diameter, third peduncle: About 2 mm. Strength: Strong. Aspect, terminal peduncle: Mostly upright. Aspect, third peduncle: About 40° from the flowering stem axis. Texture and luster: Smooth, glabrous; moderately glossy. Color: Close to 144A.

*Reproductive organs*.—Androecium: Present on disc florets only. Quantity: About five per floret. Filament length: About 2 mm. Filament color: Close to 145C. Anther size: About 0.5 mm by 2 mm. Anther shape: Narrowly oblong. Anther color: Close to 13A. Pollen amount: Scarce. Pollen color: Close to 14A. Gynoecium: Present on both ray and disc florets. Quantity: One per floret. Pistil length: About 6 mm. Style length: About 5 mm. Style color: Close to 145C. Stigma diameter: About 1 mm. Stigma shape: Cleft, decurrent. Stigma color: Close to 153C. Ovary color: Close to 145D.

*Seeds and fruits*.—To date, seed and fruit production have not been observed on plants of the new *Chrysanthemum*.

Pathogen & pest resistance: To date, plants of the new *Chrysanthemum* have not been observed to be resistant to pathogens and pests common to plants grown under commercial conditions.

Temperature tolerance: Plants of the new *Chrysanthemum* have been observed to tolerate temperatures ranging from about −12° C. to 35° C. and to be suitable for USDA Hardiness Zones 8 to 10.

It is claimed:

1. A new and distinct *Chrysanthemum* plant named 'DLFALLI5' as illustrated and described.

* * * * *